United States Patent [19]

Powell

[11] 4,255,340

[45] Mar. 10, 1981

[54] METHOD FOR PREPARING AN ALKENYL-SUBSTITUTED DICARBOXYLIC ACID ANHYDRIDE

[75] Inventor: Justin C. Powell, Wappingers Falls, N.Y.

[73] Assignee: Texaco Inc., White Plains, N.Y.

[21] Appl. No.: 70,187

[22] Filed: Aug. 27, 1979

[51] Int. Cl.$^3$ ............................................ C07D 307/60
[52] U.S. Cl. ......................... 260/346.74; 260/345.9 R
[58] Field of Search ......................... 260/346.74, 345.9

[56] References Cited

U.S. PATENT DOCUMENTS 3,935,249  1/1976  Puskas et al. .................. 260/346.74

*Primary Examiner*—Henry R. Jiles
*Assistant Examiner*—Bernard Dentz
*Attorney, Agent, or Firm*—Carl G. Ries; Robert A. Kulason; James J. O'Loughlin

[57] ABSTRACT

A method is provided for preparing an alkenyl-substituted anhydride of an unsaturated dicarboxylic acid which comprises reacting a mole of an olefin or a polyolefin having from 3 to 200 carbon atoms with from about 0.9 to 2.0 moles of an anhydride of an unsaturated dicarboxylic acid in the presence of from about 5 to about 5000 ppm, based on said polyolefin, of a brominated hydroxy compound.

13 Claims, No Drawings

METHOD FOR PREPARING AN ALKENYL-SUBSTITUTED DICARBOXYLIC ACID ANHYDRIDE

BACKGROUND OF THE INVENTION

1. Field of the Invention

Alkenyl-substituted dicarboxylic acids and their derivatives are valuable additives for fuels and for lubricating oil compositions. The basic reaction is well known and involves the reaction of a polyolefin with an unsaturated dicarboxylic acid anhydride, such as maleic anhydride, to produce the corresponding alkenyl-substituted dicarboxylic acid anhydride.

The polyolefin-dicarboxylic anhydride reaction does not proceed cleanly nor does it give theoretical results. On the contrary, the yields are less than can be desired and the reaction often results in the production of sludge or tarry residues which must be separated from the reaction product. It has been postulated that the unsaturated dicarboxylic acid anhydride reactant polymerizes and decomposes under the reaction conditions employed leading to the production of sludge or tarry residues.

2. Description of the Prior Art

Numerous processes have been developed to improve the yield of the polyolefin-dicarboxylic acid anhydride reaction. U.S. Pat. No. 3,927,041 discloses the reaction of viscous polybutenes with unsaturated aliphatic dicarboxylic acid anhydrides in the presence of a brominated dialkyl hydantoin. The use of a brominated dialkyl hydantoin is disclosed to reduce the formation of undesirable by-products resulting from polymerization and/or thermal decomposition of the unsaturated anhydrides. The use of certain dibrominated dialkyl hydantoins results in the production of an acceptable yield of alkenyl-substituted dicarboxylic acid anhydride based on the amount of the starting polymer.

U.S. Pat. No. 4,086,251 discloses a process for manufacturing a polyalkenyl succinic anhydride in the presence of an additive which suppresses the formation of tarry materials and undesirable reaction side products and/or improves yield in which a portion of the recovered unsaturated intramolecular anhydride is recycled to the reaction zone. This reference also discloses the use of reaction modifying additives including chlorinated and brominated aliphatic hydrocarbons, chlorine and/or bromine-containing derivatives of carboxylic or sulfonic acids, chlorinated and/or brominated anhydrides of aliphatic carboxylic acids, chlorinated and/or brominated aliphatic or aromatic ketones and acetals, and the above-noted dibromo-dialkyl substituted hydantoin.

SUMMARY OF THE INVENTION

It has now been discovered that the reaction between an olefin or a polyolefin having a molecular weight ranging from about 40 to 3000, and an unsaturated dicarboxylic acid anhydride can be conducted in the presence of a brominated hydroxy aliphatic compound. More specifically, the catalyst for this reaction can be a brominated aliphatic alcohol.

DESCRIPTION OF THE PREFERRED EMBODIMENTS

In accordance with the process of the invention, an olefin or a polyolefin having a molecular weight ranging from about 40 to 3000 is reacted with an unsaturated dicarboxylic acid anhydride in the presence of about 5 to 5000 ppm, based on the amount of said olefin or polyolefin of bromine in a brominated aliphatic alcohol.

A preferred class of brominated hydroxy aliphatic compounds are the brominated aliphatic alcohols represented by the formula:

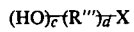

in which X is a bromine atom, R''' represents a divalent hydrocarbyl or substituted hydrocarbyl radical containing 2 to 18 carbon atoms said hydrocarbyl radical consisting of the group of alkyl, alkenyl, alkynyl, aryl, alkaryl, alkenaryl, and alkynaryl and which in the case of the substituted hydrocarbyl radicals contains hydroxy and halogen substituents and c and d have values from 1 to 6.

Examples of specific brominated aliphatic alcohols which are suitable for this reaction include 3-bromo-1-propanol, 2,3-dibromo-propanol, 4-bromo-butanol, 3-bromo-butanol, 3,4-dibromo-butanol, 2-bromoethanol, 6-bromo-hexanol, 3-bromophenyl methyl carbinol, 4-dibromophenyl cyclopropyl carbinol, 1,4-dibromo-2,3-butanediol, 2,3-dibromo-1-propanol, 1,3-dibromo-2-propanol, 1-chloro-3-bromo-2-propanol, 3-bromo-2,2-bis (bromomethyl)-1-propanol, 1,4-dibromo-2-butanol, 3-bromo-2,2-dimethyl-1-propanol, 2,3-dibromo-2-butene-1,4-diol, p-bromophenethyl alcohol, 2,2,2-tribromomethanol and 1-bromoglycerol. No brominated phenolic compounds are contemplated in this invention.

The olefin component which can be used in this process is defined as either an olefin or a polyolefin polymer. The latter is obtained by polymerizing an aliphatic olefin by known methods until a polymer is obtained within the prescribed molecular weight. Molecular weight as employed herein refers to number average molecular weight ($M_n$). The prescribed polymers are obtained by polymerizing an olefin monomer, or a mixture of olefin monomers, such as $C_2$ to $C_6$ aliphatic olefin, under known polymerization conditions to produce an olefin polymer having the required molecular weight. The preferred polyolefin polymer species are those obtained from the polymerization of propylene, isobutylene, butene-1, butene-2 or mixtures thereof to produce the corresponding polypropylene, polyisobutylenes and polybutenes. A preferred class of olefin is one having a number average molecular weight ranging from about 500 to 2000 with a particularly preferred class of olefin being a polypropylene and polyisobutylene having a molecular weight ranging from about 800 to 1500.

The unsaturated intramolecular dicarboxylic acid anhydrides which can be employed in this process include maleic anhydride, citraconic anhydride, itaconic anhydride, ethyl maleic anhydride and glutaconic anhydride.

This reaction is conducted by reacting a mole of the prescribed olefin or polyolefin with from about 0.8 to 5 moles of the unsaturated dicarboxylic acid anhydride. A more preferred mole ratio for this reaction is a mole ratio of from about 1.05 moles of olefin or polyolefin with about 2.0 moles of the prescribed anhydride. A particularly preferred mole ratio for the reaction is the ratio of about one mole of olefin or polyolefin having a molecular weight ranging from about 800 to 1500 with about 1.1 moles of maleic anhydride to produce an alkenyl succinic anhydride suitable for use as or for the preparation of a fuel or lubricating oil additive.

This reaction can be conducted at a temperature in the range from about 175° C. to 300° C. However, a preferred reaction temperature is from about 200° to 280° C. with the most preferred reaction temperature being from about 235 to 265° C.

The novel process of this invention is based on the use of the prescribed brominated aliphatic alcohol as a catalyst. This catalyst or promoter is also highly effective for reducing or minimizing the formation of a sludge or tarry residue during the course of the reaction. The catalyst is employed at a concentration ranging from about 5 to 5000 parts per million (ppm) of bromine based on the amount of olefin or polyolefin being employed in the reaction. A preferred catalyst concentration is from about 10 to 250 ppm of bromine. The manner of introducing the catalyst into the reaction is not critical. It has been found convenient, however, to mix the catalyst with the olefin or polyolefin in the prescribed proportions with the result that it is introduced into the reaction simultaneously with the polyolefin reactant in the proper concentrations.

The following examples illustrate the preparation of the alkenyl-substituted dicarboxylic acid anhydrides by the practice of this invention.

EXAMPLE I

1290 Grams of polybutene having a number average molecular weight of 1290 are added to a pressure reaction vessel equipped with a stirrer suitable for conducting the reaction under autogenous pressure. 107.9 Grams of maleic anhydride are added to the polybutene in the reactor to provide a reactant mole ratio of 1 mole of polybutene to 1.1 moles of maleic anhydride. No catalyst inhibitor is added to this comparison example.

The reaction mixture is raised to a temperature of about 245° C. and the reaction is conducted over a period of about 6 hours. The reactor is cooled and the bulk of the cooled reaction product is removed from the reactor. The reactor is then rinsed free of aliphatic hydrocarbon solubles with petroleum ether. The petroleum ether rinses and crude product are further diluted with hexane and filtered through a bed of diatomaceous earth and the filtrate evaporated free of solvents and free of unreacted maleic anhydride at a temperature up to about 150° C. and down to a pressure of about 5 mm Hg. to distill the unreacted maleic anhydride and leave the adduct and any unreacted polybutene. The reactor is rinsed again with acetone and the filter cake which is used to filter the product is extracted with acetone to leach sludge solids. The combined acetone washings are evaporated free of solvent to yield the sludge by-product.

The adduct part is analyzed by silica gel chromotography, by n.m.r. spectroscopy, by infrared spectroscopy and by saponification-titration.

In the absence of the catalyst-inhibitor, the yield of polyisobutylene-substituted maleic anhydride is 57 weight percent of the recovered product. The percent sludge found is 1.1 weight percent of the reactants charged.

EXAMPLE II

1290 Grams of polyisobutylene having a number average molecular weight of 1290 and 107.9 grams of maleic anhydride are added to a pressure reaction vessel together with 3-bromo-1-propanol at a concentration of 96 ppm based on the weight of the polyisobutylene feed. This reaction is conducted in the same manner as Example I above. 70 Weight percent of the recovered product is polyisobutenyl-substituted maleic anhydride as determined by silica gel chromotography. 6.7 grams or 0.48 weight percent of sludge is found in this reaction.

EXAMPLE III

1290 Grams of polyisobutylene having a number average molecular weight of 1290 and 107.9 grams of maleic anhydride are reacted in the presence of 96 ppm of 2,3-dibromopropanol following the procedure of Example II above. A high yield of polyisobutenyl-substituted maleic anhydride accompanied by a low production of sludge is realized.

EXAMPLE IV

1290 Grams of polyisobutylene having a number average molecular weight of 1290 and 107.9 grams of maleic anhydride are reacted in the presence of 100 ppm of 2-bromoethanol following the procedure of Example II above. A high yield of polyisobutenyl-substituted maleic anhydride accompanied by a low production of sludge is realized.

EXAMPLE V

1290 Grams of polyisobutylene having a number average molecular weight of 1290 and 107.9 grams of maleic anhydride are reacted in the presence of 90 ppm of 4-bromo-1-butanol following the procedure of Example II above. A high yield of polyisobutenyl-substituted maleic anhydride accompanied by a low production of sludge is realized.

EXAMPLE VI

1290 Grams of polyisobutylene having a number average molecular weight of 1290 and 107.9 grams of maleic anhydride are reacted in the presence of 100 ppm of 3-bromophenyl methyl carbinol following the procedure of Example II above. A high yield of polyisobutenyl-substitutd maleic anhydride accompanied by a low production of sludge is realized.

EXAMPLE VII

1290 Grams of polyisobutylene having a number average molecular weight of 1290 and 107.9 grams of maleic anhydride are reacted in the presence of 100 ppm of 3-bromo-2,2-bis(bromomethyl)-1-propanol following the procedure of Example II above. A high yield of polyisobutenyl-substituted maleic anhydride accompanied by a low production of sludge is realized.

EXAMPLE VIII

294 Grams of n-1-tetradecene, and 98.1 grams of maleic anhydride are added to a pressure reaction vessel together with 1,4-dibromo-2-butanol at a concentration of 90 ppm based on the weight of n-1-tetradecene. The mole ratio of maleic anhydride to the n-1-alkene is 1:1.

The reaction mixture is raised to a temperature of 245° C. with stirring and held under autogenous pressure for a period of about 0.45 hours after which it is cooled and removed from the reactor. The reactor is rinsed with a hydrocarbon solvent and these rinses plus the reaction mixture removed from the reactor are filtered through a bed of diatomaceous earth. The filtrate is evaporated free of solvents and free of unreacted maleic anhydride in a rotary evaporator at an elevated temperature and reduced pressure up to 125° C. at 5 mm Hg.

EXAMPLE IX (Comparison Example)

1290 Grams of polyisobutylene having a number average molecular weight of 1290 and 107.9 grams of maleic anhydride are added to a pressure reaction vessel together with pyridinium bromide perbromide at a concentration of 90 ppm based on the amount of the polyisobutylene feed. This reaction is conducted in the same manner as Example II above. 52.7 weight percent of the recovered product is polyisobutenyl-substituted maleic anhydride as determined by silica gel chromatography. 40.5 grams or 2.9 weight percent of sludge is found in this reaction.

The above examples illustrate a novel process wherein the reaction between an olefin or a polyolefin of suitable molecular weight and an unsaturated dicarboxylic acid anhydride is promoted by means of a prescribed class of halogenated hydroxy compounds or halogenated aliphatic alcohols. Relatively high yields of the alkenyl-substituted dicarboxylic acid anhydride are realized simultaneously with a marked reaction in the amount of sludge or tarry residue produced thus substantially enhancing the usefulness of this process.

I claim:

1. A method for preparing an alkenyl-substituted acid anhydride which comprises reacting an olefin or a polyolefin polymer having a number average molecular weight ranging from about 40 to 3000 with an unsaturated dicarboxylic acid anhydride at a temperture in the range from about 175° to 300° C. employing a mole ratio of from about 0.8 to 5 moles of said anhydride per mole of said olefin or polyolefin in the presence of a brominated hydroxy compound represented by the formula:

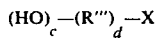

in which X is a bromine atom, R''' represents a divalent hydrocarbyl or substituted hydrocarbyl radical having from 2 to 18 carbon atoms said hydrocarbyl radical consisting of the group of alkyl, alkenyl, alkynyl, aryl, alkaryl, alkenaryl, and alkynaryl and said substituents being hydroxy and halogen and c and d are numbers from 1 to 6 with the proviso that brominated phenolic type compounds are excluded, said brominated hydroxy compound being present in an amount to provide from about 5 to 5000 ppm of bromine based on said olefin or polyolefin.

2. A method according to claim 1 in which said olefin is a polyolefin selected from the group consisting of polypropylene and polybutene having a molecular weight ranging from about 500 to 2000.

3. A method according to claim 1 in which said unsaturated carboxylic acid anhydride is selected from the group consisting of maleic anhydride, citraconic anhydride, itaconic anhydride, ethyl maleic anhydride, glutaconic anhydride and homomesaconic anhydride.

4. A method according to claim 1 in which said unsaturated carboxylic acid anhydride is maleic anhydride.

5. A method according to claim 1 in which said brominated hydroxy compound is selected from the group consisting of 3-bromo-1-propanol, 2,3-dibromo-propanol, 4-bromo-butanol, 3-bromo-butanol, 3,4-dibromo-butanol, 2-bromoethanol, 6-bromo-hexanol, 3-bromophenyl methyl carbinol, 4-dibromophenylcyclopropyl carbinol, 1,4-dibromo-2,3-butane-diol, 2,3-dibromo-1-propanol, 1,3-dibromo-2-propanol, 1-chloro-3-bromo-2-propanol, 3-bromo-2,2-bis (bromomethyl)-1-propanol, 1,4-dibromo2-butanol, 3-bromo-2,2-dimethyl-1-propanol, 2,3-dibromo-2-butene-1,4-diol, p-bromo-phenethyl alcohol, 2,2,2-tribromomethanol and 1-bromoglycerol.

6. A method according to claim 1 in which said brominated aliphatic alcohol is 3-bromophenylmethyl carbinol.

7. A method according to claim 1 in which said brominated aliphatic alcohol is 4-bromophenyl cyclopropyl carbinol.

8. A method according to claim 1 in which said brominated aliphatic alcohol is 2,3-dibromo-1-propanol.

9. A method according to claim 1 in which said brominated aliphatic alcohol is 2-bromoethanol.

10. A method according to claim 1 in which said brominated aliphatic alcohol is 3-bromo-1-propanol.

11. A method according to claim 1 in which said brominated aliphatic alcohol is 1,4-dibromo-2,3-butanediol.

12. A method according to claim 1 in which said brominated aliphatic alcohol is 1,4-dibromo-2-butanol.

13. A method according to claim 1 in which the concentration of said catalyst is from about 10 to 250 ppm of bromine based on the weight of said olefin or polyolefin.

* * * * *